United States Patent
Marker et al.

[11] Patent Number: 5,817,906
[45] Date of Patent: Oct. 6, 1998

[54] PROCESS FOR PRODUCING LIGHT OLEFINS USING REACTION WITH DISTILLATION AS AN INTERMEDIATE STEP

[75] Inventors: Terry L. Marker, Warrenville; Christopher David Gosling, Roselle, both of Ill.

[73] Assignee: UOP LLC, Des Plaines, Ill.

[21] Appl. No.: 511,332

[22] Filed: Aug. 10, 1995

[51] Int. Cl.[6] ............................... C07C 6/00; C07C 1/20
[52] U.S. Cl. ..................... 585/640; 585/638; 585/639; 585/310; 585/324; 203/28; 203/29; 203/38; 568/698; 568/699; 568/700; 568/840; 423/650; 423/651; 423/652; 423/416; 423/418.2; 423/437 R
[58] Field of Search ..................... 585/638, 639, 585/640, 310, 324; 203/28, 29, 38; 568/698, 699, 700, 840; 423/650, 651, 652, 416, 418.2, 437 R

[56] References Cited

U.S. PATENT DOCUMENTS

| | | |
|---|---|---|
| 3,326,956 | 6/1967 | Davies et al. . |
| 3,928,483 | 12/1975 | Chang et al. . |
| 4,025,575 | 5/1977 | Chang et al. . |
| 4,052,479 | 10/1977 | Chang et al. . |
| 4,076,761 | 2/1978 | Chang et al. . |
| 4,380,657 | 4/1983 | Slaugh ..................... 549/509 |
| 4,440,871 | 4/1984 | Lok et al. ................. 502/214 |
| 4,447,669 | 5/1984 | Hamon et al. ............ 585/640 |
| 4,496,786 | 1/1985 | Santilli et al. ............ 585/640 |
| 4,499,314 | 2/1985 | Seddon et al. ............ 585/408 |
| 4,543,435 | 9/1985 | Gould et al. .............. 585/330 |
| 4,547,616 | 10/1985 | Avidan et al. ............ 585/640 |
| 4,677,242 | 6/1987 | Kaiser ...................... 585/638 |
| 4,677,243 | 6/1987 | Kaiser ...................... 585/638 |
| 4,843,183 | 6/1989 | Inui ......................... 585/640 |
| 4,861,938 | 8/1989 | Lewis et al. .............. 585/640 |
| 4,973,792 | 11/1990 | Lewis et al. .............. 585/638 |
| 5,012,031 | 4/1991 | Schleppinghoff et al. ...... 585/639 |
| 5,073,236 | 12/1991 | Gelbein et al. ............ 203/29 |
| 5,095,163 | 3/1992 | Barger ..................... 585/640 |
| 5,126,308 | 6/1992 | Barger et al. ............ 502/214 |
| 5,177,114 | 1/1993 | Van Dijk et al. ......... 518/703 |
| 5,191,141 | 3/1993 | Barger et al. ............ 585/640 |
| 5,214,217 | 5/1993 | Knifton ................... 568/618 |
| 5,214,218 | 5/1993 | Knifton ................... 568/698 |

FOREIGN PATENT DOCUMENTS

| | | |
|---|---|---|
| 0 407 038 A1 | 1/1991 | European Pat. Off. . |
| WO 93/13013 | 7/1993 | WIPO . |

OTHER PUBLICATIONS

Holm–Larsen, H. Presented at the 1994 World Methanol Conference, Geneva, Switzerland, Nov. 30–Dec. 1, 1994, *Selection of Technology for Large Methanol Plants*.

*Methanol Production and Use*, Cheng, W. H. and Kung, H. H. Ed., 1994, pp. 111–113.

Peters et al., Plant Design and Economics for Chemical Engineers, Third Edition, pp. 6–7, 1980.

*Primary Examiner*—Elizabeth D. Wood
*Attorney, Agent, or Firm*—Thomas K. McBride; John G. Tolomei; Richard P. Silverman

[57] ABSTRACT

The present invention relates to a process for the production of light olefins comprising olefins having from 2 to 4 carbon atoms per molecule from a crude oxygenate feedstock. The crude oxygenate feedstock comprises an alcohol, and water. The process comprises passing the crude oxygenate feedstock to catalyst to a distillation with reaction zone to convert the alcohol to an ether and produce an ether product having a reduced water relative to the crude oxygenate feedstock and a first water stream. The ether product is passed to an oxygenate conversion zone containing a metal aluminosilicate catalyst to produce a light olefin stream. The use of crude oxygenate feedstock, having a high proportion of water, combined with a process for producing additional water in the conversion of the alcohol to an ether, actually reduces the amount of water contacted with the water sensitive, metal alumino-silicate catalyst in the oxygenate conversion zone which provides the advantage of extended catalyst life and greater catalyst stability in the oxygenate conversion zone.

15 Claims, 1 Drawing Sheet

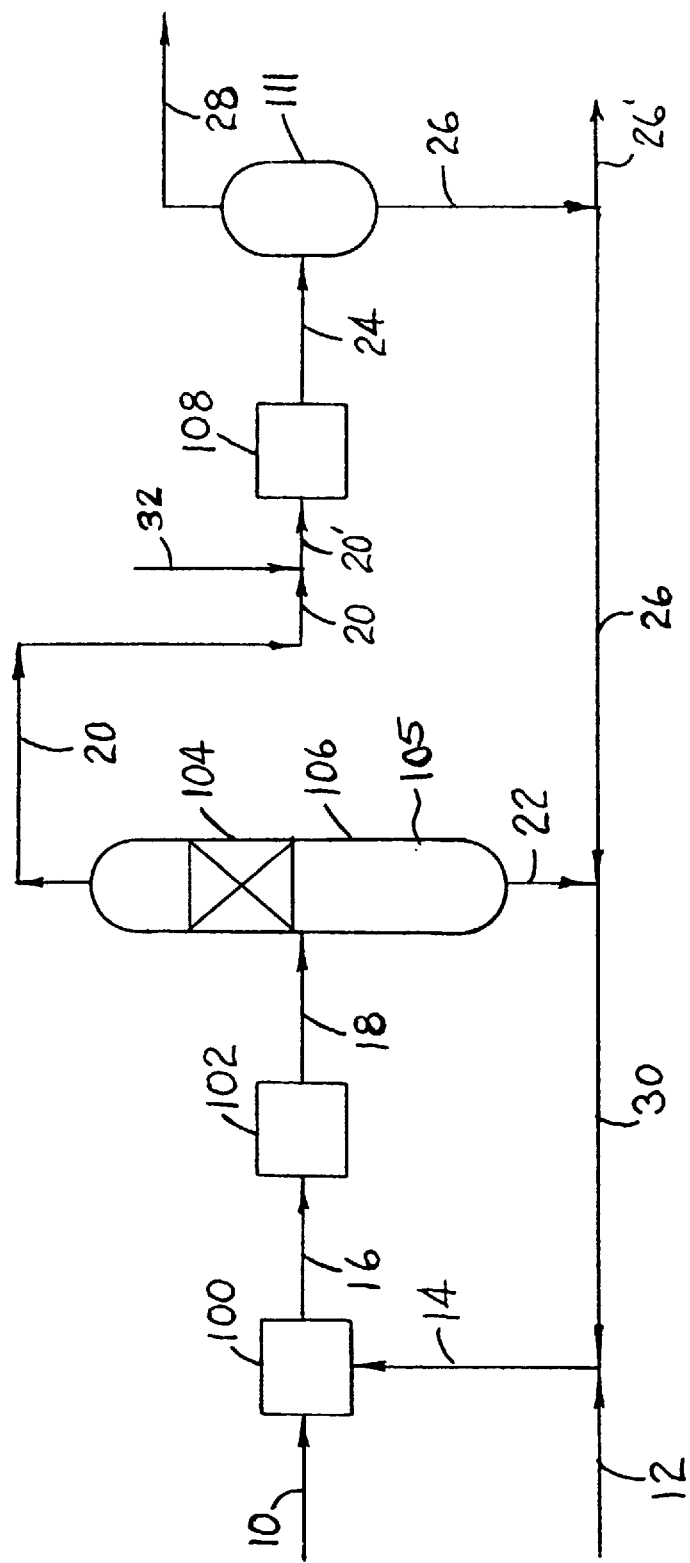

PROCESS FOR PRODUCING LIGHT OLEFINS USING REACTION WITH DISTILLATION AS AN INTERMEDIATE STEP

FIELD OF THE INVENTION

This invention relates to a process for the production of light olefins from an oxygenate feedstream.

BACKGROUND OF THE INVENTION

Light olefins have traditionally been produced through the process of steam or catalytic cracking. Because of the limited availability and high cost of petroleum sources, the cost of producing light olefins from such petroleum sources has been steadily increasing. Light olefins serve as feeds for the production of numerous chemicals. As the emerging economies of the Third World strain toward growth and expansion, the demand for light olefins will increase dramatically.

The search for alternative materials for light olefin production has led to the use of oxygenates such as alcohols, and more particularly to the use of methanol, ethanol, and higher alcohols or their derivatives. These alcohols may be produced by fermentation or from synthesis gas. Synthesis gas can be produced from natural gas, petroleum liquids, and carbonaceous materials including coal, recycled plastics, municipal wastes, or any organic material. Thus, alcohol and alcohol derivatives may provide non-petroleum based routes for the production of olefin and other related hydrocarbons.

Molecular sieves such as the microporous crystalline zeolite and non-zeolitic catalysts, particularly silicoaluminophosphates (SAPO), are known to promote the conversion of oxygenates to hydrocarbon mixtures. Numerous patents describe this process for various types of these catalysts: U.S. Pat. Nos. 3,928,483, 4,025,575, 4,252,479 (Chang et al.); 4,496,786 (Santilli et al.); 4,547,616 (Avidan et al.); 4,677,243 (Kaiser); 4,843,183 (Inui); 4,499,314 (Seddon et al.); 4,447,669 (Harmon et al.); 5,095,163 (Barger); 5,191,141 (Barger); 5,126,308 (Barger); 4,973,792 (Lewis); and 4,861,938 (Lewis).

The process may be generally conducted in the presence of one or more diluents which may be present in the oxygenate feed in an amount between about 1 and about 99 molar percent, based on the total number of moles of all feed and diluent components fed to the reaction zone (or catalyst). Diluents include—but are not limited to—helium, argon, nitrogen, carbon monoxide, carbon dioxide, hydrogen, water, paraffins, hydrocarbons (such as methane and the like), aromatic compounds, or mixtures thereof. U.S. Pat. Nos. 4,861,938 and 4,677,243 particularly emphasize the use of a diluent combined with the feed to the reaction zone to maintain sufficient catalyst selectivity toward the production of light olefin products, particularly ethylene. The above U.S. Patents are hereby incorporated by reference.

U.S. Pat. No. 4,543,435 discloses a process for converting an oxygenate feedstock comprising methanol, dimethyl ether or the like in an oxygenate conversion reactor into liquid hydrocarbons comprising $C_2$–$C_4$ olefins and $C_5^+$ hydrocarbons. The $C_2$–$C_4$ olefins are compressed to recover an ethylene-rich gas. The ethylene-rich gas is recycled to the oxygenate conversion reactor. U.S. Pat. No. 4,076,761 discloses a process for converting oxygenates to gasoline with the return of a hydrogen-rich gaseous product to a synthesis gas plant or the oxygenate conversion reaction zone.

U.S. Pat. No. 5,177,114 discloses a process for the conversion of natural gas to gasoline grade liquid hydrocarbons and/or olefins by converting the natural gas to a synthesis gas, and converting the synthesis gas to crude methanol and/or dimethyl ether and further converting the crude methanol/dimethyl ether to gasoline and olefins.

EPO publication No. 0407038A1 to Smith discloses a method for producing dialkyl ether comprising feeding a stream containing an alkyl alcohol to a distillation column reactor and therein contacting the stream with a fixed bed solid acidic catalyst to form the corresponding dialkyl ether and water and concurrently fractionating the ether product from the water and unreacted material. Smith discloses that both the ether product and the water must be removed to force the reaction to completion and that one mole of water is produced for each mole of dialkyl ether formed, which dilutes the reaction system.

International Patent Application No. 93/13013 to Kvisle et al. relates to an improved method for producing a silicon-alumino-phosphate catalyst which is more stable to deactivation by coking. The patent discloses that after a period of time, all such catalysts used to convert methanol to olefins (MTO) lose the active ability to convert methanol to hydrocarbons primarily because the microporous crystal structure is coked; that is, filled up with low volatility carbonaceous compounds which block the pore structure. The carbonaceous compounds can be removed by conventional methods such as combustion in air.

It has been found that high concentrations of water in the reaction mixture, which are generally required to maintain an appropriate level of dilution, have an adverse effect on the catalyst life and cause the catalyst to deactivate rapidly. Furthermore, water is a by-product of the reaction and its production increases the amount of water seen by the catalyst. Processes are sought which reduce the amount of water in the reaction mixture while maintaining the appropriate level of dilution. These and other disadvantages of the prior art are overcome by the present invention, however, and a new improved process for conversion of oxygenates to hydrocarbons is provided.

SUMMARY OF THE INVENTION

In the present invention, a combination of water production processes is employed to reduce the amount of water at a critical point in the production of light olefins. It was discovered that the use of water or steam as a diluent in an oxygenate conversion process had a deleterious effect on the metal aluminophosphate catalyst. By the process of the present invention, the water in the oxygenate conversion zone is significantly reduced and significant capital and operating cost savings are obtainable. In not removing water from the crude oxygenate feedstock and further subjecting the crude oxygenate feedstock to a secondary conversion step for the production of additional water, the catalyst life and stability of the metal aluminosilicate catalyst in the oxygenate conversion zone can be improved. By retaining the effluent from the carbon oxide conversion zone as a crude oxygenate stream, a significant capital and operating cost saving over providing the conventional oxygenate purification facilities in the carbon oxide conversion zone is achieved. Such purification facilities are well known in the industry and generally described in a book titled, *Methanol Production and Use*, edited by Wattsun Cheng and Harold H. Kung, Marcel Dekker, Inc., 1994, pages 111–113 and hereby incorporated by reference. The cost of such water separation equipment in a conventional world scale methanol plant typically ranges from 10 to 12 percent of the cost of the entire methanol plant.

The invention provides a process for the production of light olefins comprising olefins having from 2 to 4 carbon atoms per molecule from crude oxygenate feedstock. The crude oxygenate feedstock comprises an alcohol and water. The process comprises passing the crude oxygenate feedstock to a distillation with reaction zone containing an acid catalyst to produce an ether product stream having a reduced water content relative to the crude oxygenate feedstock and a first water stream. The ether product stream is passed in the presence of a diluent to an oxygenate conversion zone containing a metal aluminophosphate catalyst to produce a light olefm stream comprising said light olefins and water. The light olefin stream is passed to a water separation zone to provide a light olefm product stream and a second water stream.

In a further embodiment, the present invention is a process for the production of light olefins having 2 to 4 carbon atoms per molecule from a hydrocarbon feedstream comprising methane. The process comprises reacting a first water stream and said hydrocarbon feedstream in a syngas production zone to produce a syngas stream comprising hydrogen and a carbon oxide. The syngas stream is passed to a carbon oxide conversion zone to produce a crude oxygenate feedstream comprising methanol and water. The crude oxygenate feedstream is passed to a distillation with reaction zone to produce an ether stream having a reduced water content relative to the crude oxygenate feedstream and a second water stream. The ether stream is passed in the presence of a diluent to an oxygenate conversion zone to produce a light olefin stream comprising light olefins and water. The light olefin stream is separated to provide a light olefin product stream and a third water stream. At least a portion of the third water stream is admixed with at least a portion of the second water stream to provide a water recycle stream. The water recycle stream is combined with a make-up water stream to provide the first water stream.

BRIEF DESCRIPTION OF THE DRAWINGS

The figure is a schematic process flow diagram illustrating the process of the instant invention employing a reaction with distillation step.

DETAILED DESCRIPTION OF THE INVENTION

A carbon oxide, as used herein, refers to carbon dioxide and/or carbon monoxide. Synthesis gas refers to a combination of hydrogen and carbon oxides produced in a synthesis gas plant from a hydrocarbon gas derived from natural gas or from the partial oxidation of petroleum or coal residues. Generally, the production of oxygenates, primarily methanol, takes place as a combination of three process steps and a utility section. The three process steps are: synthesis gas preparation, methanol synthesis, and methanol distillation. In the synthesis gas preparation step, the hydrocarbon feedstock is purified to remove sulfur and other potential catalyst poisons prior to being converted into synthesis gas. The conversion to synthesis gas generally takes place at high temperatures over a nickel-containing catalyst to produce a synthesis gas containing a combination of hydrogen, carbon monoxide, and carbon dioxide. Typically, the pressure at which the synthesis gas is produced ranges from about 20 to about 75 bar and the temperature at which the synthesis gas exits the reformer ranges from about 700° C. to about 1100° C. The synthesis gas contains a molar ratio of hydrogen to carbon oxide ranging from about 2 to about 3, and more typically the molar ratio of hydrogen to carbon oxide varies from about 2.0 to about 2.3. The synthesis gas is subsequently compressed to a methanol synthesis pressure. In the methanol synthesis step, the compressed synthesis gas is converted to methanol, water, and minor amounts of by-products.

The synthesis gas preparation, also known as reforming, may take place in a single-step wherein all of the energy consuming reforming reactions are accomplished in a single tubular steam reformer. The single-step reformer results in a production of surplus hydrogen and a substantial heat surplus. In a preferred alternative, the synthesis gas preparation may take place in a two-step reforming process wherein the primary reforming in a tubular steam reformer is combined with an oxygen-fired secondary reforming step which produces a synthesis gas with a deficiency in hydrogen. With this combination it is possible to adjust the synthesis gas composition to the most suitable composition for methanol synthesis. As an alternative, autothermal reforming -wherein a stand-alone, oxygen-fired reformer produces synthesis gas having a hydrogen deficiency followed by the downstream removal of carbon dioxide to restore the desired ratio of hydrogen to carbon oxide—results in a simplified process scheme with lower capital cost. The burner design is an important part of either oxygen-fired step. The burner mixes the hydrocarbon and oxygen and by combustion in the flame, heat is provided for conversion of the hydrocarbons.

The reaction from synthesis gas to oxygenates such as methanol is an exothermic reaction which is favored by low temperature and high pressure over a heterogeneous catalyst. The reactions which produce methanol exhibit a decrease in volume. As disclosed in U.S. Pat. No. 3,326,956, low-pressure methanol synthesis is based on a copper oxide-zinc oxide-alumina catalyst that typically operates at a nominal pressure of 5–10 MPa and temperatures ranging from about 150° C. to about 450° C. over a variety of catalysts, including $CuO/ZnO/Al_2O_3$, $CuO/ZnO/Cr_2O_3$, $ZnO/Cr_2O_3$, Fe, Co, Ni, Ru, Os, Pt, and Pd. Catalysts based on ZnO for the production of methanol and dimethyl ether are preferred. The low-pressure, copper-based methanol synthesis catalyst is commercially available from suppliers such as BASF, ICI Ltd. of the United Kingdom, and Haldor-Topsoe. Methanol yields from copper-based catalysts are generally over 99.5% of the converted $CO+CO_2$ present as methanol in the crude product stream. Water is a by-product of the conversion of the synthesis gas to oxygenates. A paper entitled, "Selection of Technology for Large Methanol Plants," by Helge Holm-Larsen, presented at the 1994 World Methanol Conference, Nov. 30–Dec. 1, 1994, in Geneva, Switzerland, and herein incorporated by reference, reviews the developments in methanol production and shows how further reduction in costs of methanol production will result in the construction of very large plants with capacities approaching 10,000 metric tonnes per day.

In the present invention, a distillation with reaction zone is provided to convert methanol to dimethyl ether (DME). The distillation with reaction zone contains a reaction zone wherein a catalyst is retained in the conventional manner as disclosed in U.S. Pat. No. 5,073,236 to A. P. Gelbein which is incorporated herein by reference for its teaching as to the structure and usage of these catalytic packing systems. These devices provide a means to evenly distribute the catalyst and reactants uniformly within the desired locations in the overall vessel. The apparatus is also very effective at promoting vapor-liquid contacting and, therefore, fractional distillation of the product(s) from the reactants.

Advantages attributed to the catalytic distillation concept, wherein reaction products are continuously separated from the reactants and removed from the reaction zone by fractional distillation performed concurrently with the reaction, include a decrease in the capital cost of the plant needed to perform the process, the ability to achieve a higher degree of conversion, and the ability to perform processes which formerly were performed only in a batch type operation on a continuous basis. These advantages result from performing the reaction in a separation zone capable of removing the reaction products from the reactants and catalyst. Hence it is only necessary to provide one primary vessel and the reaction is not limited by chemical equilibrium. An acid catalyst employed in reaction zone 106 facilitates the conversion of methanol to dimethyl ether (DME). Suitable catalysts for the conversion of methanol to DME include, but are not limited to, macroporous acid forms of sulfonic ion-exchange resins such as the sulfonated styrene-divinyl benzene resin described in U.S. Pat. No. 2,922,822. Suitable resins are available commercially. The macroporous structure of a suitable resin is described in detail in U.S. Pat. No. 5,012,031 as having a surface area of at least 400 $m^2/g$, a pore volume of 0.6–2.5 ml/g and a mean pore diameter of 40–1000 angstroms. A particularly suitable and preferred acid catalyst is sold under the designation Amberlyst 15 and Amberlyst 35 by Rohm and Haas. It is also contemplated that non-resin acid catalysts such as the zeolitic and treated clay based catalysts disclosed in U.S. Pat. Nos. 5,214,217 and 5,214,218 and in European Patent Publication 528628 based on application 93-060453/08 for an HF modified Y zeolite catalyst are employed in the present invention. Of the zeolite catalysts, zeolites such as zeolite Y and zeolite B are preferred. Another suitable catalyst for the conversion of methanol to DME is disclosed in U.S. Pat. No. 4,380,657 wherein an amorphous silica-alumina catalyst is employed. The above-mentioned U.S. Pat. Nos. 2,922,822; 4,380,657; 5,012,031; 5,214,217 and 5,214,218 are hereby incorporated by reference. The acid catalyst of the distillation with reaction zone of the present invention is selected from the group consisting of ion-exchange resins, amorphous silica-alumina, zeolite Y and zeolite B. The DME conversion conditions include a pressure in the range of about 140 kPa (20 psia) to about 7 MPa (1000 psia) and a temperature in the range of about 80 to about 250° C.

In accordance with the process of the present invention, an oxygenate feed is catalytically converted to hydrocarbons containing aliphatic moieties such as—but not limited to—methane, ethane, ethylene, propane, propylene, butylene, and limited amounts of other higher aliphatics by contacting the oxygenate feedstock with a preselected catalyst. The oxygenate feedstock comprises hydrocarbons containing aliphatic moieties such as —but not limited to—alcohols, ethers, and carbonyl compounds or mixtures thereof. The aliphatic moiety preferably contains from about 1 to about 10 carbon atoms, and more preferably 1 to about 4 carbon atoms. Representative oxygenates include—but are not limited to—methanol, isopropanol, n-propanol, ethanol, fuel alcohols, dimethyl ether, diethyl ether, formaldehyde, dimethylketone, and acetic acid having alkyl groups of 1 to 10 carbon atoms or mixtures thereof. In a preferred embodiment, methanol and/or dimethyl ether is used as the oxygenate feedstock. In a more preferred embodiment, dimethyl ether (DME) is used as the oxygenate feedstock. The water concentration in the oxygenate conversion zone may be reduced by the use of an oxygenate feedstock comprising an ether, such as DME, rather than an alcohol, such as methanol. For example, the ratio of methyl groups to oxygen in DME is twice that of methanol, resulting in the production of half of the production of water for the same amount of light olefin produced. The term "oxygenate feedstock" as employed in the present invention and described herein designates only the organic material used as the feed. The term "crude oxygenate feedstock" as employed in the present invention refers to the crude reactor effluent such as from a methanol plant which comprises, methanol, DME, heavier alcohols, and a significant amount of water. Preferably, the content of water in the crude oxygenate feedstock ranges from about 10 to about 50 weight percent and more preferably ranges from about 15 to about 25 weight percent based on the amount of methanol present in the crude oxygenate feedstock. The total charge of feed to the oxygenate conversion zone may contain additional compounds such as diluents.

A diluent is required in the oxygenate conversion zone to maintain the selectivity of the catalyst to produce light olefins, particularly ethylene and propylene. Examples of diluents which may be used are helium, argon, nitrogen, carbon monoxide, carbon dioxide, hydrogen, steam, paraffinic hydrocarbons, (e.g., methane), aromatic hydrocarbons, (e.g., benzene, toluene), and mixtures thereof. The amount of diluent used can vary considerably and is usually from about 5 to about 90 mole percent of the feedstock and preferably from about 25 to about 75 mole percent.

The oxygenate conversion process of the present invention is preferably conducted in the vapor phase such that the oxygenate feedstock is contacted in a vapor phase in the oxygenate conversion zone with a molecular sieve catalyst at effective process conditions to produce hydrocarbons, i.e., an effective temperature pressure, WHSV and, optionally, an effective amount of diluent, correlated to produce hydrocarbons. The process is affected for a period of time sufficient to produce the desired light olefin products. In general, the residence time employed to produce the desired product can vary from seconds to a number of hours. It will be readily appreciated that the residence time will be determined to a significant extent by the reaction temperature, the molecular sieve selected, the WHSV, the phase (liquid or vapor) and process design characteristics selected. The feedstock flow rate affects olefin production. Increasing the feedstock flow rate (expressed as weight hourly space velocity, or WHSV) enhances the formation of olefin production relative to paraffin production. However, the enhanced olefin production relative to paraffin production is offset by a diminished conversion of oxygenate to hydrocarbons.

The oxygenate conversion zone is operated over a wide range of pressures, including autogenous pressures. At pressures between about 0.001 atmospheres (0.76 torr) and about 1000 atmospheres (760,000 torr), the formation of light olefin products will be affected although the optimum amount of product will not necessarily form at all pressures. The preferred pressure is between about 0.01 atmospheres (7.6 torr) and about 100 atmospheres (76,000 torr). More preferably, the pressure of the oxygenate conversion zone will range from about 0.1 to about 10 atmospheres. The pressures referred to herein for the process are exclusive of the inert diluent, if any, that is present and refer to the partial pressure of the feedstock as it relates to oxygenate compounds and/or mixtures thereof. Pressures outside the stated range are not excluded from the scope of this invention, although such do not fall within certain desirable embodiments of the invention. At the lower and upper end of the pressure range and beyond, the selectivities, conversions and/or rates to light olefin products may not occur at the optimum, although light olefin such as ethylene may still be formed.

The temperature which may be employed in the oxygenate conversion zone may vary over a wide range depending, at least in part, on the selected molecular sieve catalyst. In general, the process can be conducted at an effective temperature between about 200° C. (392° F.) and about 700° C. (1292° F.). Temperatures outside the stated range are not excluded, although they do not fall within certain desirable embodiments of the present invention. At the lower end of the temperature range, and thus, generally at a lower rate of reaction, the formation of the desired light olefin products may become markedly slow. At the upper end of the temperature range and beyond, the oxygenate conversion zone may not form an optimum amount of light olefin products. Notwithstanding these factors, the reaction will still occur and the feedstock, at least in part, can be converted to the desired light olefin products at temperatures outside the range between about 200° C. (392° F.) and about 700° C. (1292° F.).

The present invention where an aliphatic hetero compounds are converted into light olefins, it is preferred that the oxygenate conversion zone catalysts have relatively small pores. The preferred small pore catalysts are defined as having pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane and most preferably by adsorption of n-hexane (average kinetic diameter of about 0.43 nm) and negligible adsorption of isobutane. Negligible adsorption of a given adsorbate is adsorption of less than three percent by weight of the catalyst and adsorption of the adsorbate is over three percent by weight of the adsorbate based on the weight of the catalyst. Certain of the catalysts useful in the present invention have pores with an average effective diameter of less than 5 Angstroms. The average effective diameter of the pores of preferred catalysts is determined by measurements described in D. W. Breck, *ZEOLITE MOLECULAR SIEVES* by John Wiley & Sons, New York (1974), hereby incorporated by reference in its entirety. The term effective diameter is used to denote that occasionally the pores are irregularly shaped, e.g., elliptical, and thus the pore dimensions are characterized by the molecules that can be adsorbed rather than the actual dimensions. Preferably, the small pore catalysts have a substantially uniform pore structure, e.g., substantially uniformly sized and shaped pore. Suitable catalyst may be chosen from among layered clays, zeolitic molecular sieves, and non-zeolitic molecular sieves.

Zeolitic molecular sieves in the calcined form may be represented by the general formula:

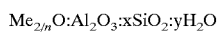

where Me is a cation, x has a value from about 2 to infinity, n is the cation valence and y has a value of from about 2 to 10.

Typically, well-known zeolites which may be used include chabazite—also referred to as Zeolite D, clinoptilolite, erionite, faujasite—also referred to as Zeolite X and Zeolite Y, ferrierite, mordenite, Zeolite A, Zeolite P, ZSM-5, ZSM-11, and MCM-22. Other zeolites include those having a high silica content, i.e., those having silica to alumina ratios greater than 10 and typically greater than 100 can also be used. One such high silica zeolite is silicalite, as the term used herein includes both the silicapolymorph disclosed in U.S. Pat. No. 4,061,724 and also the F-silicate disclosed in U.S. Pat. No. 4,073,865, hereby incorporated by reference. Detailed descriptions of some of the above identified zeolites may be found in D. W. Breck, supra.

Non-zeolitic molecular sieves include molecular sieves which have the proper effective pore size and are embraced by an empirical chemical composition, on an anhydrous basis, expressed by the empirical formula:

where EL is a metal selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1. When EL is a mixture of metals, x represents the total amount of the metal mixture present. Preferred metals (EL) are silicon, magnesium and cobalt with silicon being especially preferred.

The preparation of various ELAPOs are well known in the art and may be found in U.S. Pat. Nos. 5,191,141 (ELAPO); 4,554,143 (FeAPO); 4,440,871 (SAPO); 4,853,197 (MAPO, MnAPO, ZnAPO, COAPO); 4,793,984 (CAPO), 4,752,651 and 4,310,440 all of which are incorporated by reference. Generally, the ELAPO molecular sieves are synthesized by hydrothermal crystallization from a reaction mixture containing reactive sources of EL, aluminum, phosphorus and a templating agent. Reactive sources of EL are the metal salts such as the chloride and nitrate salts. When EL is silicon, a preferred source is fumed, colloidal or precipitated silica. Preferred reactive sources of aluminum and phosphorus are pseudo-boehmite alumina and phosphoric acid. Preferred templating agents are amines and quaternary ammonium compounds. An especially preferred templating agent is tetraethylammonium hydroxide (TEAOH).

The reaction mixture is placed in a sealed pressure vessel, optionally lined with an inert plastic material such as polytetrafluoroethylene and heated preferably under autogenous pressure at a temperature between about 50° C. and 250° C. and preferably between about 100° C. and 200° C. for a time sufficient to produce crystals of the ELAPO molecular sieve. Typically the time varies from about 2 hours to about 30 days and preferably from about 4 hours to about 20 days. The desired product is recovered by any convenient method such as centrifugation or filtration.

It is known that the particle size of the ELAPO molecular sieve can be reduced by stirring the reaction mixture at high speeds (see examples) and by using TEAOH as the templating agent. It is preferred that the ELAPO molecular sieves are composed of particles at least 50% of which have a particle size less than 1.0 μm and no more than 10% of the ELAPO particles have a particle size greater than 2.0 μm.

The ELAPOs which are synthesized using the process described above will usually contain some of the organic templating agent in its pores. In order for the ELAPOs to be active catalyst, the templating agent in the pores must be removed by heating the ELAPO powder in an oxygen containing atmosphere at a temperature of about 200° C. to about 700° C. until the template is removed, usually a few hours.

A preferred embodiment of the invention is one in which the metal (EL) content varies from about 0.005 to about 0.05 mole fraction. If EL is more than one metal, then the total concentration of all the metals is between about 0.005 and 0.05 mole fraction. An especially preferred embodiment is one in which EL is silicon (usually referred to as SAPO). The SAPOs which can be used in the instant invention are any of those described in U.S. Pat. Nos. 4,440,871; 5,126,308, and 5,191,141. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 Å. Another SAPO structure, SAPO-17, as exemplified in Examples 25 and 26 of the '871 patent, is also preferred. The SAPO-17 structure is characterized in that it adsorbs oxygen, hexane, and water but does not adsorb isobutane, indicating that it has a pore opening of greater than about 4.3 Å and less than about 5.0 Å.

The preferred ELAPO catalyst may be, and preferably is, incorporated into solid particles in which the catalyst is present in an amount effective to promote the desired hydrocarbon conversion. In one aspect, the solid particles comprise a catalytically effective amount of the catalyst and at least one matrix material, preferably selected from the group consisting of binder materials, filler materials, and mixtures thereof to provide a desired property or properties, e.g., desired catalyst dilution, mechanical strength, and the like to the solid particles. Such matrix materials are often, to some extent, porous in nature and may or may not be effective to promote the desired hydrocarbon conversion. The matrix materials may promote conversion of the feedstream and often provide reduced selectivity to the desired product or products relative to the catalyst. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, aluminophosphates, mixtures of these and the like.

If matrix materials, e.g., binder and/or filler materials, are included in the catalyst composition, the non-zeolitic and/or zeolitic molecular sieves preferably comprise about 1% to 99%, more preferably about 5% to about 90% and still more preferably about 10% to about 80%, by weight of the total composition. The preparation of solid particles comprising catalyst and matrix materials is conventional and well known in the art and, therefore, need not be discussed in detail herein.

During the oxygenate conversion reaction, a carbonaceous material, i.e., coke is deposited on the catalyst. The carbonaceous deposit material has the effect of reducing the number of active sites on the catalyst which thereby affects the extent of the conversion. During the conversion process a portion of the coked catalyst is withdrawn from the reaction zone and regenerated to remove at least a portion of the carbonaceous material and returned to the oxygenate conversion reaction zone. Depending upon the particular catalyst and conversion, it can be desirable to substantially remove the carbonaceous material e.g., to less than 1 wt %, or only partially regenerate the catalyst, e.g., to from about 2 to 30 wt % carbon. Preferably, the regenerated catalyst will contain about 0 to 20% and more preferably from about 0 to 10% carbon. Additionally, during regeneration there can be oxidation of sulfur and in some instances nitrogen compounds along with the removal of metal materials from the catalyst. Moreover, regeneration conditions can be varied depending upon catalyst used and the type of contaminant material present upon the catalyst prior to its regeneration. The details concerning the conditions for regeneration are known to those skilled in the art and need to be further disclosed herein.

DETAILED DESCRIPTION OF THE DRAWINGS

The process of the present invention is hereinafter described with reference to the drawing which illustrates various aspects of the process. It is to be understood that no limitation to the scope of the claims which follow is intended by the following description. Those skilled in the art will recognize that these process flow diagrams have been simplified by the elimination of many necessary pieces of process equipment including some heat exchangers, process control systems, pumps, fractionation systems, etc. It may also be discerned that the process flow depicted in the drawing may be modified in many aspects without departing from the basic overall concept of the invention.

With reference to the Figure, a hydrocarbon feedstream comprising methane such as natural gas, or gas derived from coal, shale oil, residua or combination thereof is passed by line 10 to a synthesis gas plant 100. A water stream is passed to the synthesis plant in stream 14. The synthesis gas plant 100 conventionally operates at a reaction temperature ranging from about 700° C. –1100° C., a pressure ranging from about 20–80 bar, and a water to carbon molar ratio from about 2.0 to about 3.5 to provide a synthesis gas stream 16. Optionally (not shown), this ratio may be varied according to the carbon monoxide shift reaction:

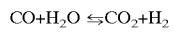

$$CO + H_2O \leftrightarrows CO_2 + H_2$$

over a copper/zinc oxide catalyst in the conventional manner. The synthesis gas stream 16 is passed via line 16 to a carbon oxide conversion zone 102. A crude oxygenate feedstock comprising methanol and/or dimethyl ether and water is withdrawn from the carbon oxide conversion zone 102 in line 18. The crude oxygenate feedstock may contain from about 10 to about 50 mol-% water and preferably contains from about 15 to 35 mol-% water. The crude oxygenate feedstock is passed to a distillation with reaction zone 106. The distillation with reaction zone 106 contains a reaction zone 104 and a distillation zone 105 wherein an acid catalyst is retained. As the DME conversion takes place, an ether product comprising DME and having a reduced amount of water relative to the crude oxygenate feedstream is removed in line 20 and concurrently, a second water stream is produced and removed in line 22. The energy provided by the heat of reaction of the alcohol, such as methanol, in the conversion over the acid catalyst is employed to reboil the distillation zone 106 to separate the ether product and unreacted alcohol from the water stream which is removed from the bottom of the distillation with reaction zone. The reaction zone 104 may be present at any point in the distillation zone 105. For this separation, it is preferred that the reaction zone 104 be located at a point above the point where the crude oxygenate feedstock is introduced to the distillation with reaction zone 106. In this manner, excess water in the crude oxygenate feedstock is at least partially removed in the distillation zone 105 prior to entering the reaction zone 104. This synergy provides a further advantage in reduced capital and utility costs for the invention over a conventional scheme wherein separate oxygenate purification equipment, an intermediate DME reactor, and a separate DME/water separation column would be required. The ether product stream 20 admixed with a diluent 32 such as an olefin having 3–5 carbon atoms per molecule and the ether/diluent admixture 20' is passed via lines 20 and 20' to an oxygenate conversion zone 108 for the production of light olefins. Preferably, the diluent is selected from the group consisting of propylene and butylene, and most preferably, the diluent comprises butylene. The oxygenate conversion zone 108 is maintained at a reaction temperature ranging from about 350° C. to about 525° C. and a pressure of about 1 to about 5 atmospheres. The oxygenate conversion zone contains a molecular sieve catalyst such as a metal aluminosilicate catalyst for the conversion of at least a portion of the oxygenate feedstock into $C_2$–$C_4$ olefins Preferably, the oxygenate conversion zone 108 contains an ELAPO catalyst selected from the group consisting of SAPO-34, SAPO-17, and mixtures thereof. The ether product stream admixed with the diluent in line 20' is introduced to the oxygenate conversion reaction zone containing a fluidized bed of the molecular sieve catalyst in the presence of a diluent such as steam or other inert material. As the reaction proceeds, a carbonaceous deposit is formed on the ELAPO catalyst forming a coked catalyst which has a lower level of activity than fresh catalyst. A portion of the coked catalyst is removed from the fluidized bed, stripped of volatile material, regenerated, and returned to the oxygenate conversion zone. The effluent from the oxygenate conversion zone 108 is withdrawn in line 24 and passed to a water separation zone 111. In the water separation zone 111 a light olefin product stream 28 is separated from a third water stream 26. The light olefin product stream comprises ethylene, propylene, and butylene. In a further embodiment not shown in the Figure, the light olefin products: ethylene, propylene, and butylene are separated in a conventional manner by fractionation and at least a portion of either the propylene or butylene product is returned to the oxygenate conversion zone 108 as the diluent. It was discovered that the $C_3$–$C_5$ olefins do not react further in the oxygenate conversion zone and can thus be employed as diluents. By returning at least a portion of the $C_3$–$C_5$ olefins to the oxygenate conversion zone as a diluent, the process has the advantage of supplying the diluent from the products of the reaction without the requirement for additional equipment for separation and recompression of the diluent. At least a portion of the third water stream 26 is combined with at least a portion of the second water stream 22 to provide a recycle water stream 30. The recycle water stream 30 is admixed with a make-up water stream in line 12 to provide the first water stream in line 14. A portion of the water recirculated in this manner may be withdrawn as a drag stream 26' which is sent to water treatment facilities (not shown) to minimize the build-up of contaminants within the process.

The addition of the DME conversion step in reaction zone 106 produced additional water; however, it also provided a means for removing both the water remaining in the crude oxygenate feedstream and the water produced in the conversion of methanol to DME. Furthermore, the use of DME in the oxygenate conversion zone 111 results in less water produced during the formation of the light olefins which further reduces the amount of water present to the metal aluminosilicate catalyst in zone 111.

The following examples are only used to illustrate the present invention and are not meant to be limiting.

EXAMPLES

Example I

A series of runs to determine the effect of accelerated hydrothermal aging on the catalyst of the present invention was carried out. The aged catalyst was evaluated to determine the effect of the aging on the catalyst activity. A 40 gram sample of SAPO-34 catalyst was placed in a 2.2 cm (⅞ inch) I.D. tubular monel reactor forming a catalyst bed therein. The reactor was fitted with stainless steel sintered frits at the bottom of the catalyst bed and on the reactor outlet above the catalyst bed. An air purge flowing up from the bottom to the top of the catalyst bed was established to fluidize the catalyst bed. The pressure was increased to about 793 kPa (100 psig) and the temperature was raised from room temperature to about 460° C. When the temperature stabilized, the air flow was replaced with water at a rate of about 90 grams/hour. The steaming of the catalyst in this manner continued for a series of specified times ranging from about 5 hours to about 200 hours. At the end of the specified time, the water flow was replaced with air and the reactor was cooled to about 100° C. and depressurized.

A portion of the fresh and hydrothermally aged catalyst of approximately 10 grams each was loaded into a 2.2 cm (⅞ inch) I.D., porcelain-lined stainless steel reactor. The catalyst sample was pre-treated with flowing nitrogen at about 435° C. for about 1 hour to dry the catalyst and raise the temperature of the catalyst bed. The nitrogen was replaced with a mixture of methanol and water containing about 80 wt% methanol at a feed rate of about 12.5 grams per hour and at a pressure of about 138 kPa (5 psig). The time, or on-stream time, from the start of the reaction to the point at which the conversion of methanol (and DME) dropped to 99% was recorded. The performance of the catalyst was monitored using an on-line GC measuring the composition of the reactor effluent. The results of this accelerated hydrothermal aging are shown in Table 1. The hydrothermal aging of the SAPO-34 catalyst showed a progressive loss in catalyst life ranging from about 4.8 hours for fresh catalyst to about 3.5 hours for a catalyst sample after 100 hours of steaming.

TABLE 1

| HYDROTHERMAL AGING TESTS OF SAPO-34 HOURS ON STREAM AT >99% CONVERSION | |
|---|---|
| FRESH CATALYST | 4.8 |
| 5 HOURS STEAMING | 4.5 |
| 25 HOURS STEAMING | 4.3 |
| 100 HOURS STEAMING | 3.5 |

Example II

The evaluation of the effect of the accelerated hydrothermal aging on conversion for the fresh catalyst and the 100 steaming hour samples of Example I was continued. The conversion was recorded as a function of time from the introduction of the feed. The effect of the continued hydrothermal aging of the catalyst is shown in Table 2. For the fresh catalyst and the 100 hour aged catalyst, the conversion dropped to about 20% after on-stream times ranging from about 5 to about 6.3 hours, with the steamed catalyst exhibiting a more pronounced reduction in conversion at an earlier on-stream time than the feed catalyst. Although the accelerated hydrothermal testing showed that steaming the catalyst results in the permanent loss of catalyst activity, this steaming was evaluated at levels well beyond water levels which would normally be encountered when water or steam is employed as a diluent.

TABLE 2

EFFECT OF STEAMING ON MTO CATALYST

| CONVERSION, % | FRESH CATALYST | 100 HOURS AGING |
|---|---|---|
| 99 | 4.8 | 3.5 |
| 50 | 5.7 | 4.5 |
| 20 | 6.3 | 5.2 |

Example III

A 10 gram sample of fresh SAPO-34 catalyst was loaded into the 2.2 cm I.D. stainless steel reactor of Example I. The catalyst was preheated with flowing nitrogen at about 435° C. for about 1 hour to dry the catalyst and raise the temperature of the catalyst bed to about 435° C. The nitrogen was replaced with a mixture of methanol and water in a molar ratio of 1.00 to 0.44 at a pressure of about 138 kPa (5 psig) and at a weight hourly space velocity (WHSV) of about 2.5 hr$^{-1}$. As in Example I, the catalyst life, or the time from the start of the reaction to the point at which the conversion of methanol declined to 99%, was recorded and the selectivities at 99% were measured. The catalyst life and the selectivities at 99% conversion are reported in Table 3, column A. The reported catalyst life at 99% methanol conversion was 2.4 hr with the methanol/water feed mixture.

TABLE 3

EFFECT OF PROPYLENE RECYCLE ON SAPO-34

|  | A | B |
|---|---|---|
| CATALYST LIFE, hrs | 2.4 | 4.5 |
| SELECTIVITY @ 99% CONVERSION | | |
| Ethylene | 53.8 | 52.7 |
| Propylene | 29.2 | 29.1 |
| Butylene | 7.8 | 9.5 |
| $C_2^-/C_3^-$ | 1.85 | 1.81 |

Example IV

Another 10 gram sample of fresh catalyst was charged to the reactor of Example III. The catalyst was preheated with nitrogen to a temperature of 435° C. for 1 hour and then replaced with a feed containing methanol, water, and propylene with the following molar ratio 1.00/1.17/0.17 and at a space velocity of about 1.7 hr$^{-1}$. As in Example III, the catalyst life and selectivities were measured at the point when the conversion declined to 99%. The Example IV results are shown in Table 3, column B.

A comparison of the data in Table 4 for the use of water diluent (A) with the use of diluent comprising propylene (B) showed that the substitution of a portion of the water with propylene did not change the selectivity for the production of ethylene, propylene or butylene. Furthermore, the ratio of ethylene to propylene in Example III and Example IV have essentially the same ethylene and propylene selectivity at 99% conversion, and the molar ratio of ethylene to propylene produced is essentially the same. The catalyst life improved with the propylene to the amount of methanol contacted with the catalyst. Thus, propylene may be employed as a diluent for the oxygenate conversion reaction zone without further conversion of the propylene. It is believed that the presence of propylene outside of the SAPO-34 structure apparently acts as an inert in the oxygenate conversion process.

We claim:

1. A process for the production of light olefins having 2 to 4 carbon atoms per molecule from a crude oxygenate feedstock comprising an alcohol and water, said process comprising:
    a) introducing said crude oxygenate feedstock at a temperature of about 80 to about 250° C. and a pressure of about 140 kPa to about 7 MPa to a catalytic distillation zone containing a reaction zone and a distillation zone to remove a first water stream from the catalytic distillation zone, said reaction zone being above a point where the crude oxygenate feedstock is introduced to the catalytic distillation zone, said reaction zone containing an acid catalyst to produce an ether product stream having a reduced water content relative to said crude oxygenate feedstock;
    b) passing the ether product in the presence of a diluent at effective conditions to an oxygenate conversion zone containing a metal aluminophosphate catalyst to produce a light olefin stream comprising said light olefins and water; and
    c) passing said light olefin stream to a water separation zone to provide a light olefin product stream and a second water stream.

2. The process of claim 1 wherein said metal aluminophosphate catalyst is characterized by an empirical composition on an anhydrous basis by the formula:

$$(EL_xAl_yP_z)O_2$$

where EL is a metal selected from the group consisting of silicon, magnesium, zinc, iron, cobalt, nickel, manganese, chromium, and mixtures thereof, x is the mole fraction of EL and is at least 0.005, y is the mole fraction of Al and is at least 0.01, and z is the mole fraction of P and is at least 0.01 and x+y+z=1.

3. The process of claim 2, wherein said metal aluminophosphate is selected from the group consisting of SAPO-34, SAPO-17, and mixtures thereof.

4. The process of claim 1 wherein said crude oxygenate feedstock comprises about 15 mol-% to about 35 mol-% water.

5. The process of claim 1 wherein said ether product comprises dimethyl ether.

6. The process of claim 1 wherein said oxygenate feedstock is selected from the group of methanol, ethanol, propanol, and mixtures thereof.

7. The process of claim 1 wherein said light olefin product comprises ethylene, propylene, and butylene.

8. The process of claim 1 wherein the acid catalyst of said distillation with reaction zone is selected from the group consisting of ion-exchange resins, amorphous silica-alumina, zeolite Y, and zeolite B.

9. The process of claim 1 wherein the diluent comprises a $C_3$–$C_5$ olefin.

10. The process of claim 9 wherein the diluent comprises propylene.

11. The process of claim 9 wherein the diluent comprises butylene.

12. The process of claim 1 further comprising separating said light olefin stream into an ethylene product, a propylene product, and a butylene product.

13. The process of claim 12 further comprising returning at least a portion of said propylene product as said diluent.

14. The process of claim 12 further comprising returning at least a portion of said butylene product as said diluent.

15. A process for the production of light olefins having 2 to 4 carbon atoms per molecule from a hydrocarbon feedstream comprising methane said process comprising:

a) reacting a first water stream and said hydrocarbon feedstream in a syngas production zone to produce a syngas stream comprising hydrogen and a carbon oxide;

b) passing the syngas stream to a carbon oxide conversion zone to produce a crude oxygenate feedstock comprising methanol and water;

c) introducing said crude oxygenate feedstock at a temperature of about 80 to about 250° C. and a pressure of about 140 kPa to about 7 MPa to a catalytic distillation zone containing a reaction zone and a distillation zone said reaction zone being above a point where the crude oxygenate feedstock is introduced to the catalytic distillation zone, said reaction zone containing an acid catalyst to produce a dimethyl ether stream having a reduced water content relative to said crude oxygenate feedstream and a second water stream;

d) passing said dimethyl ether stream at effective conditions and in the presence of a diluent to an oxygenate conversion zone containing a metal aluminophosphate catalyst to produce a light olefin stream comprising said light olefins and water; and e) separating said light olefin stream to provide a light olefin product stream and a third water stream and admixing at least a portion of said third water stream and at least a portion of said second water stream to provide a water recycle stream and combining said water recycle stream with a make-up water stream to provide said first water stream.

* * * * *